US00PP26485P2

(12) United States Plant Patent
Jones

(10) Patent No.: US PP26,485 P2
(45) Date of Patent: Mar. 8, 2016

(54) ***DIASCIA* PLANT NAMED 'SUNJODI 042'**

(50) Latin Name: *Diascia hybrida*
Varietal Denomination: Sunjodi 042

(71) Applicant: Jimmy Jones, Netherwent (GB)

(72) Inventor: Jimmy Jones, Netherwent (GB)

(73) Assignee: Suntory Flowers LTD., Tokyo (JP)

( * ) Notice: Subject to any disclaimer, the term of this patent is extended or adjusted under 35 U.S.C. 154(b) by 169 days.

(21) Appl. No.: 13/999,244

(22) Filed: Jan. 31, 2014

(51) Int. Cl.
*A01H 5/02* (2006.01)

(52) U.S. Cl.
USPC ..... Plt./425

(58) Field of Classification Search
USPC ..... Plt./425
See application file for complete search history.

*Primary Examiner* — Anne Grunberg
(74) *Attorney, Agent, or Firm* — C. A. Whealy

(57) ABSTRACT

A new and distinct cultivar of *Diascia* plant named 'Sunjodi 042', characterized by its semi-upright and mounding plant habit; strong flowering stems; early and long flowering period; numerous large white and pink-colored flowers; and good garden performance.

1 Drawing Sheet

Botanical designation: *Diascia hybrida.*
Cultivar denomination: 'SUNJODI 042'.

BACKGROUND OF THE INVENTION

The present invention relates to a new and distinct cultivar of *Diascia* plant, botanically known as *Diascia hybrida* and hereinafter referred to by the name 'Sunjodi 042'.

The new *Diascia* plant is a product of a planned breeding program conducted by the Inventor in St. Brides, Netherwent, Monmouthshire, United Kingdom. The objective of the breeding program is to create new freely flowering *Diascia* plants with strong flowering stems and large attractive flowers.

The new *Diascia* plant originated from a cross-pollination conducted by the Inventor on Jun. 7, 2008 in St. Brides, Netherwent, Monmouthshire, United Kingdom of a proprietary selection of *Diascia hybrida* identified as code number D5768, not patented, as the female, or seed, parent and with a proprietary selection of *Diascia hybrida* identified as code number D899, not patented, as the male, or pollen, parent. The new *Diascia* plant was discovered and selected by the Inventor as a single flowering plant from within the progeny of the stated cross-pollination in a controlled greenhouse environment in St. Brides, Netherwent, Monmouthshire, United Kingdom on Aug. 20, 2008.

Asexual reproduction of the new *Diascia* plant by vegetative cuttings in a controlled greenhouse environment in St. Brides, Netherwent, Monmouthshire, United Kingdom since Aug. 20, 2008 has shown that the unique features of this new *Diascia* plant are stable and reproduced true to type in successive generations.

SUMMARY OF THE INVENTION

Plants of the new *Diascia* have not been observed under all possible combinations of environmental conditions and cultural practices. The phenotype may vary somewhat with variations in environmental conditions such as temperature and light intensity without, however, any variance in genotype.

The following traits have been repeatedly observed and are determined to be the unique characteristics of 'Sunjodi 042'. These characteristics in combination distinguish 'Sunjodi 042' as a new and distinct *Diascia* plant:

1. Semi-upright and mounding plant habit.
2. Strong flowering stems.
3. Early and long flowering period.
4. Numerous large white and pink-colored flowers.
5. Good garden performance.

Plants of the new *Diascia* can be compared to plants of the female parent selection. Plants of the new *Diascia* differ primarily from plants of the female parent selection in the following characteristics:

1. Plants of the new *Diascia* have longer flowering stems than plants of the female parent selection.
2. Plants of the new *Diascia* have larger flowers than plants of the female parent selection.

Plants of the new *Diascia* can be compared to plants of the male parent selection. Plants of the new *Diascia* differ primarily from plants of the male parent selection in cold hardiness as plants of the new *Diascia* are more cold hardy than plants of the male parent selection.

Plants of the new *Diascia* can be compared to plants of the *Diascia hybrida* 'Sunjodipi', disclosed in U.S. Plant Pat. No. 24,870. In side-by-side comparisons conducted in St. Brides, Netherwent, Monmouthshire, United Kingdom, plants of the new *Diascia* differed primarily from plants of 'Sunjodipi' in the following characteristics:

1. Plants of the new *Diascia* were larger than plants of 'Sunjodipi'.
2. Plants of the new *Diascia* had smaller leaves than plants of 'Sunjodipi'.
3. Plants of the new *Diascia* had fewer flowers per inflorescence but more flowers per plant than plants of 'Sunjodipi'.
4. Plants of the new *Diascia* and 'Sunjodipi' differed in flower color as plants of 'Sunjodipi' had light red purple-colored flowers.

BRIEF DESCRIPTION OF THE PHOTOGRAPHS

The accompanying colored photographs illustrate the overall appearance of the new *Diascia* plant showing the colors as true as it is reasonably possible to obtain in colored reproductions of this type. Colors in the photographs may differ slightly from the color values cited in the detailed botanical description which accurately describe the colors of the new *Diascia* plant.

The photograph at the top of the sheet is a top perspective view of a typical flowering plant of 'Sunjodi 042' grown in a container.

The photograph at the bottom of the sheet is a close-up view of a typical flowering plant of 'Sunjodi 042'.

DETAILED BOTANICAL DESCRIPTION

The aforementioned photographs and following observations, measurements and values describe plants grown in 15-cm containers in an outdoor nursery in Higashiomi, Shiga, Japan and under cultural practices typical of commercial *Diascia* production. During the production of the plants, day temperatures averaged 23° C. and night temperatures averaged 13° C. Plants were four months old when the description was taken and five months old when the photographs were taken. In the following description, color references are made to The Royal Horticultural Society Colour Chart, 2007 Edition, except where general terms of ordinary dictionary significance are used.

Botanical classification: *Diascia hybrida* 'Sunjodi 042'.

Parentage:

*Female, or seed, parent.*—Proprietary selection of *Diascia hybrida* identified as code number D5768, not patented.

*Male or pollen parent.*—Proprietary selection of *Diascia hybrida* identified as code number D899, not patented.

Propagation:

*Type.*—By vegetative cuttings.

*Time to produce a rooted young plant, summer.*—About two weeks at temperatures about 18° C.

*Time to produce a rooted young plant, winter.*—About 18 days at temperatures about 18° C.

*Root description.*—Fibrous; white in color.

*Rooting habit.*—Freely branching.

Plant description:

*Plant form and growth habit.*—Semi-upright plant habit; vigorous growth habit; freely branching habit with numerous lateral branches developing per plant.

*Plant height.*—About 34.9 cm.

*Plant diameter* (*area of spread*).—About 59.6 cm.

Lateral branch description:

*Length.*—About 24.4 cm.

*Diameter.*—About 2.4 mm.

*Internode length.*—About 2.3 cm.

*Texture.*—Sparsely pubescent; longitudinally ridged.

*Color.*—Close to 143B.

Leaf description:

*Arrangement.*—Opposite, simple.

*Length.*—About 2.5 cm.

*Width.*—About 1.7 cm.

*Shape.*—Triangular.

*Apex.*—Acute.

*Base.*—Truncate.

*Margin.*—Serrate.

*Texture, upper surface.*—Smooth, glabrous.

*Texture, lower surface.*—Rugose, glabrous.

*Venation pattern.*—Pinnate.

*Color.*—Developing leaves, upper surface: Close to 137C. Developing leaves, lower surface: Close to 138B. Fully expanded leaves, upper surface: Close to 137A; venation, close to 137A. Fully expanded leaves, lower surface: Close to 138B; venation, close to 138B.

*Petioles.*—Length: About 2 mm. Diameter: About 2.9 mm. Texture, upper and lower surfaces: Sparsely pubescent. Color, upper and lower surfaces: Close to 144B.

Flower description:

*Flower arrangement and habit.*—Large single flowers arranged on terminal and axillary racemes; flowers zygomorphic with five lobes fused at the base and spurred; freely flowering habit with about eight to ten flowers per raceme and about 163 flowers developing per plant; flowers face outwardly.

*Fragrance.*—None detected.

*Flowering response and natural flowering season.*—Early flowering habit, plants begin flowering about three weeks after planting; long flowering period, plants flower freely and continuously from May to October in Japan.

*Flower longevity.*—Flowers last about five days on the plant; flowers not persistent.

*Inflorescence height.*—About 8.4 cm.

*Inflorescence diameter.*—About 3 cm.

*Flower diameter.*—About 1.45 cm by 1.53 cm.

*Flower depth.*—About 5 mm.

*Flower buds.*—Length: About 5.6 mm. Diameter: About 4.1 mm. Shape: Spherical. Color: Close to NN155C; towards the base, close to 70C.

*Corolla.*—Arrangement: Corolla consists of five petals modified into two upright banner petals, two lateral petals and a larger lower lip petal. Banner lobe length: About 4.8 mm. Banner lobe width: About 7 mm. Lateral lobe length: About 5.7 mm. Lateral lobe width: About 6.1 mm. Lower lobe length: About 9.2 mm. Lower lobe width: About 9.5 mm. Banner and lateral lobes shape: Orbicular. Lower lobe shape: Broadly ovate. Banner, lateral and lower lobes apex: Rounded. Banner, lateral and lower lobes margin: Entire. Banner, lateral and lower petals texture, upper and lower surfaces: Smooth, glabrous. Spur length: About 5.9 mm. Spur diameter: About 5.4 mm. Spur orientation: Positioned towards the flower or pointed inwardly. Color, banner, lateral and lower petals: When opening, upper surface: Close to NN155C; towards the base of the banner and lateral petals, close to 63A to 63B; towards the base of the basal petal, close to 4C. When opening, lower surface: Close to NN155D; towards the base of the banner and lateral petals, close to 63A to 63C. Fully opened, upper surface: Close to NN155C; towards the base of the banner and lateral petals, close to 63A to 63B; towards the base of the basal petal, close to 4D. Fully opened, lower surface: Close to NN155D; towards the base of the banner and lateral petals, close to 63A to 63C. Spur: Between 63C and NN155D; towards the apex, close to 61A.

*Sepals.*—Appearance: Five sepals fused into a star-shaped calyx. Length: About 1.8 mm. Width: About 1.2 mm. Shape: Lanceolate. Apex: Acute. Margin: Entire. Texture, upper and lower surfaces: Smooth, glabrous. Color, immature and mature, upper surface: Close to 144B. Color, immature and mature, lower surface: Close to 144B.

*Peduncles.*—Length: About 2.9 cm. Diameter: About 1.6 mm. Angle: Mostly erect to outwardly. Texture: Sparsely pubescent. Color: Close to 143A.

*Pedicels.*—Length: About 6.8 mm. Diameter: About 0.3 mm. Angle: About 45° from the peduncle axis. Texture: Sparsely pubescent. Color: Close to 163C tinted with close to 60C.

*Reproductive organs.*—Androecium: Stamen number per flower: About four. Stamen length: About 2.6 mm. Anther shape: Bi-lobed, elliptic. Anther size: About 1 mm by 1.2 mm. Anther color: Close to 17B. Amount of pollen: Scarce. Pollen color: Close to 8A. Gynoecium: Pistil number per flower: One. Pistil length: About 2.7 mm. Style length: About 1.8 mm. Stigma shape: Orbicular. Stigma color: Close to 144C. Ovary color: Close to 144B.

*Seeds and fruits.*—Seed and fruit production have not been observed on plants of the new *Diascia.*

Garden performance: Plants of the new *Diascia* have been observed to have good garden performance and to tolerate wind, rain and temperatures ranging from about 5° C. to about 35° C.

Pathogen & pest resistance: Plants of the new *Diascia* have not been observed to be resistant to pests and pathogens common to *Diascia* plants.

It is claimed:

1. A new and distinct *Diascia* plant named 'Sunjodi 042' as illustrated and described.

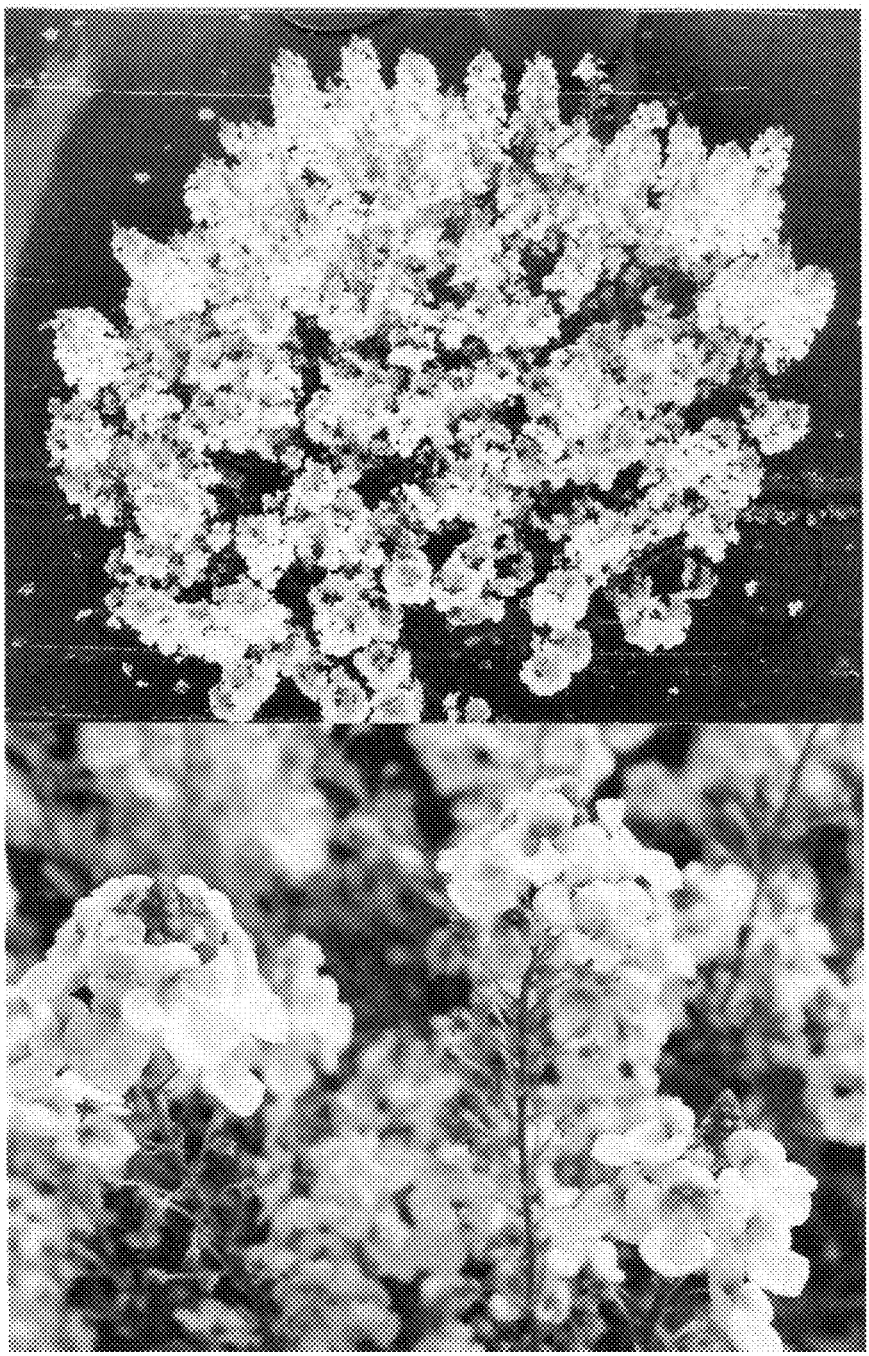

* * * * *